United States Patent [19]

Kveglis et al.

[11] Patent Number: 4,971,626

[45] Date of Patent: Nov. 20, 1990

[54] SEMI-POLAR HYPERDISPERSANTS FOR PIGMENT BASES

[75] Inventors: Albert A. Kveglis, Pine Brook; Arnold H. Gruben, Cedar Grove, both of N.J.

[73] Assignee: Sun Chemical Corporation, Fort Lee, N.J.

[21] Appl. No.: 406,985

[22] Filed: Sep. 14, 1989

Related U.S. Application Data

[60] Division of Ser. No. 337,509, Apr. 13, 1989, Pat. No. 4,882,436, which is a continuation-in-part of Ser. No. 190,632, May 5, 1988, abandoned.

[51] Int. Cl.$^5$ .................... C09D 11/02; C09D 253/14
[52] U.S. Cl. ........................................ 106/23; 106/22; 106/499; 548/354
[58] Field of Search ............................ 106/22, 23, 499; 548/354

[56] References Cited

U.S. PATENT DOCUMENTS

| | | | |
|---|---|---|---|
| Re. 32,411 | 5/1987 | Hutter | 525/167.5 |
| 3,884,713 | 5/1975 | Langley et al. | 106/499 |
| 4,028,128 | 6/1977 | Robertson | 106/23 |
| 4,224,212 | 9/1980 | Topham | 524/190 |

*Primary Examiner*—William R. Dixon, Jr.
*Assistant Examiner*—Helene Klemanski
*Attorney, Agent, or Firm*—Jack Matalon

[57] ABSTRACT

Quaternized oligourethanes, useful as dispersing agents in preparing high-solids pigment concentrates for use in manufacturing inks, especially inks intended for use in gravure and packaging applications. The novel oligourethanes are prepared by reacting an appropriate ester or alcohol with a hydroxyethylimidazoline and polyisocyanate followed by quaternization with acids or alkyl derivatives of acids.

5 Claims, No Drawings

SEMI-POLAR HYPERDISPERSANTS FOR PIGMENT BASES

This is a divisional of copending application Ser. No. 07/337,509, filed on April 13, 1989, now U.S. Pat. No. 4,882,436.

This application is a continuation-in-part of co-pending application Ser. No. 190,623, filed May 5, 1988 and now abandoned.

This invention relates to quaternized oligourethanes which are useful as dispersing agents in preparing high solids pigment concentrates for use in the manufacture of inks, especially inks intended for use in gravure and packaging applications.

BACKGROUND OF THE INVENTION

Due to the economics of the ink business today, it is highly desirable to be able to process pigments into high-solids concentrates. Typically, such concentrates would contain from 30 to 60% pigment. Ideally, they could be let down in a wide variety of vehicles in order to produce a wide range of finished inks.

The economic advantages offered by such concentrates are twofold. First, they would greatly reduce the inventory of intermediates which must be carried by an ink plant. Only one intermediate dispersion would be needed for each pigment versus the several which are now typically used. Second, energy consumption would be considerably reduced. The higher the pigment concentration at which dispersion can be effected, the less the total volume of material that must be processed through a mill and therefore the less total energy consumed in processing the pigment.

Traditionally, vehicles for lithographic inks are composed of alkyd resins and/or rosin derivatives and/or hydrocarbon resins, together with high-boiling hydrocarbon solvent. It is known in the art that satisfactory dispersions containing 30 to 60% pigment cannot be prepared using such traditional vehicle components alone. Usually mixtures at such solids levels cannot be processed in standard milling equipment. In the few cases where they can be processed, they yield dispersions with unacceptable rheological properties, i.e. dispersions which cannot be pumped or otherwise conveniently transferred from one vessel to another. Such dispersions usually also show inferior color development and poor aging stability.

Recently attempts have been made to overcome the above-described problems by using compounds which are better dispersants for pigments than are the traditional alkyd resins and rosin derivatives. For example, U.S. Pat. No. 4,224,212 describes the use of dispersing agents attained by reacting a poly (lower alkylene) imine with a polyester having free carboxylic acid groups to form reaction products containing at least two polyester chains attached to each poly (lower alkylene) imine chain. Preferred polyesters are the polyesters of an hydroxy carboxylic acid of the formula HO—R—COOH where R is a divalent aliphatic radical containing at least 8 carbon atoms in which there are at least 4 carbon atoms between the hydroxy and carboxylic acid groups. Preferred polyesters are also the polyesters formed from a mixture of aforementioned hydroxy carboxylic acids with a carboxylic acid which is free from hydroxy groups.

U.S. Pat. No. 4,415,705 describes the use of rosin derivatives as dispersants. These dispersants are attained by reacting a poly (lower alkylene) imine having a molecular weight of 1,000 to 15,000 with a polyester obtained by esterifying hydroxy stearic acid or its oligomer, with tall oil rosin. This patent states that such dispersants have been found to be superior to products made from wood rosin or gum rosin.

SUMMARY OF THE INVENTION

A novel class of quaternized oligourethanes has been discovered. These quaternized oligourethanes have been found to be very useful in preparing non-flocculating dispersions of high loadings of inorganic or organic pigments or dyestuffs. Such dispersions have been found to produce inks which yield excellent results especially when such inks are utilized for gravure and packaging applications.

DETAILS OF THE PRESENT INVENTION

The novel quaternized oligourethanes of the present invention may be represented by the formula:

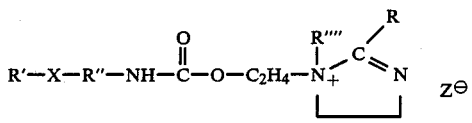

wherein X represents the radical

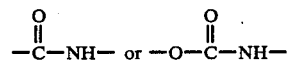

such that when X is

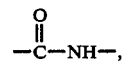

R' is an ester resulting from the reaction of a $C_2$-$C_{18}$ hydroxyalkanoic acid or a $C_3$-$C_{18}$ hydroxyalkenoic acid and rosin, and when X is

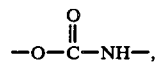

R' is a $C_3$-$C_{18}$ linear or branched alkyl, phenyl, alkaryl, aralkyl, cycloalkyl or the radical

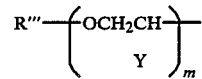

wherein Y is hydrogen or methyl, R''' is a $C_1$-$C_6$ alkyl and m is an integer of 1 to 20;

R is a $C_{11}$-$C_{17}$ linear or branched alkyl, alkenyl, alkynyl or cycloalkyl;

R'' is a $C_6$-$C_{14}$ linear or branched alkyl, phenyl, alkaryl, aralkyl or cycloalkyl or a dimer or trimer thereof;

R'''' is hydrogen or a $C_1$-$C_4$ linear or branched alkyl; and

Z is R'''''$OSO_3$, Cl, Br, I, $NO_3$ R'''''$SO_3$, (R''''')$_{3-n}$H$_n$PO$_4$ or (R''''')$_{3-n}$H$_n$PO$_3$ wherein n is an integer of 0 to 3, and R''''' is phenyl, $CF_3$, $C_1$-$C_4$ linear or branched alkyl or $C_7$-$C_{12}$ aralkyl or alkaryl.

The rosin which is used for reaction with hydroxyalkanoic acid or hydroxyalkenoic acid may be wood rosin, gum rosin or tall oil rosin, but tall oil rosin is preferred.

Preferably, in the general formula given above, X is a urethane radical i.e.

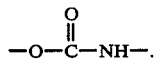

Preferably the ester is that which results from the reaction of a $C_6-C_{18}$ hydroxy alkanoic acid with tall oil rosin.

In the above general formula, it is preferred that R' be the radical

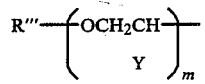

wherein Y is hydrogen or methyl, R''' is a $C_1-C_6$ alkyl, preferably a $C_2-C_4$ alkyl and m is an integer of 1 to 20, preferably 2 to 10. It is also preferred that R'' be a $C_7-C_{13}$ aralkyl or alkaryl and Z be R''''$OSO_3$.

The quaternized oligourethanes are excellent dispersing agents for dispersing solid materials in organic liquids. The dispersion can be obtained by any of the conventional and well known methods of preparing dispersions. Thus the solid, the organic liquid and the dispersing agent may be mixed in any order and the mixture then subjected to a mechanical treatment to reduce the particle size of the solid, for example by ball milling, bead milling, gravel milling or plastic milling until the dispersion is formed.

Alternatively, the solid can be treated to reduce its particle size independently or in admixture with either the organic liquid or the dispersing agent, and the other ingredient or ingredients then added following which dispersion can be obtained by stirring the mixture. A dispersion obtained in this way and comprising the solid in finely divided form and one or more dispersing agents is a further feature of this invention.

The amount of dispersing agent present in the dispersion is generally in the range of 1–20 wt. %, based on the weight of the dispersion. The dispersion generally contains 30–75 wt. % of the solid material and 10–50 wt. % of the organic liquid, based on the weight of the dispersion. It may also be helpful to incorporate up to 5 wt. %. based on the weight of the dispersion, of a nonionic surfactant such as sorbitol monooleate, glycerol monooleate, polyethylene glycol mono nonyl phenyl ether, poly(ethylene-co-propylene)glycol mono octyl phenyl ether, ethoxylated sorbitan esters, long chain fatty acid esters of polyethyleneglycol, lecithin, tertiary acetylenic diols, etc. The solid may be any particulate solid material of an inorganic or organic nature which is substantially insoluble in the organic liquid at the desired temperature of usage and which is capable of comminution into a finely divided form. This invention is of particular value when the solid is a pigment or dyestuff. For the purposes of this invention, the term "pigment" includes both inorganic and organic pigments and also lakes and toners.

As examples of organic pigments there may be mentioned azo, thionindigo, anthraquinone, anthanthrone and isodibenzanthrone pigments, vat dye pigments, triphenodioxazine pigments phthalocyanine pigments for example copper phthslocyanine, its nuclear chlorinated derivatives and cooper tetraphenyl or octaphenyl phthalocyanine and other heterocyclic pigments, for example linear quinacridone.

As examples of inorganic pigments there may be mentioned chrome pigments including the chromates of lead, zinc, barium and calcium and various mixtures and modifications such as are commercially available as pigments of greenish-yellow to red shades under the names primrose, lemon, middle orange, scarlet and red chromes. Modified chrome pigments may contain for example sulphate radicals and/or additional metals such as aluminium, molybdenum and tin. Further examples of inorganic pigments are carbon black, titanium dioxide, zinc oxide, Prussian Blue and its mixtures with chrome yellows which are known as Brunswick Greens or chrome greens, cadmium sulphide and sulphoselenide, iron oxides, vermilion and ultramarine. These and various other pigments suitable for use in the present invention are described in Volume 2 of "Colour Index 6 2nd Edition," published jointly in 1956 by the Society of Dyers and Colourists and the American Association of Textile Chemists and Colourists, under the heading of "Pigments" and in subsequent authorized amendments thereto.

The term "lake" denotes a water-insoluble metal salt or complex of an organic dyestuff which has been precipitated on a water-insoluble inorganic substrate such as alumina.

The term "toner" denotes a water-insoluble metal salt or complex, in particular a calcium or barium salt or complex, of a soluble or sparingly soluble organic dyestuff, in particular an azo dyestuff, which has optionally been prepared in the presence of an extender such as rosin.

As specific examples of the said lakes and toners there may be mentioned the barium toner of 1-(2'-sulpho-4'-methyl-5'-chlorophenylazo)-2-hydroxy-3-naphthoic acid, the nickel complex of 3-(4'-chlorophenylazo)-quinoline-2,4-diol, the rosinated barium toner of 1-(2'-sulpho-4'-chloro-5'-methylphenylazo)-2-naphthol, the aluminium lake of 1,4-dihydroxyanthraquinone-2-sulphonic acid and, above all, a rosinated calcium toner of 1-(2'-sulpho-4'-methylphenylazo)-2-hydroxy-3-naphthoic acid.

Especially preferred pigments for use in the present invention are those typically employed for gravure and packaging ink systems such as diarylide yellow, BON Red, carbon black, Red Lake C, Lithol Rubine, phthalocyanine blue, phthalocyanine green, molybdenum orange and titanium dioxide.

Dyestuffs which are useful in the present invention are those which are water soluble or water-insoluble such as basic, acid and direct dyestuffs. The dyestuffs include azo types such as monoazo and diazo and metal derivatives thereof, anthraquinone, nitro, phthalocyanine, methine, styryl, naphthoperinore, quinaphthalone, diarylmethane, triarylmethane, xanthine, azine, oxazine and thiazine dyestuffs. If desired the dyestuffs can be reactive dyestuffs which contain groups capable of forming covalent bonds with textile materials.

Any organic liquid may be used in the dispersion but hydrocarbons are preferred. As examples of such liquids there are mentioned aromatic hydrocarbons such as benzene, toluene, xylene, aliphatic and cycloaliphatic hydrocarbons such as petroleum fractions, white spirit and cyclohexane, and high boiling mineral oils such as spindle oil. Alternative organic liquids are halogen substituted hydrocarbons such as chlorobenzene, trichloroethylene, perchloroethylene, 1,1,1-trichloroethane, methylene dichloride, chloroform, 1,1,2-trichloro-1,2,2-trifluoroethane, carbon tetrachloride, tetrachloroethane or dibromoethylene and mixtures of these compounds, esters such as ethyl acetate, propyl acetate and butyl acetate and heat bodied linseed oils used as lithographic varnish media and ketones such as methylethylketone methylisobutyl ketone and cyclohexanone. Mixtures of such solvents may be used. The solvents may contain other materials in solution, for example the alkyd, nitrocellulose, acrylic, urea/formaldehyde, melamine/formaldehyde or other resins used in paint media or zinc/calcium rosinates used in gravure ink media. Especially preferred solvents are aliphatic hydrocarbons which are compatible with gravure and packaging ink systems, such as hexanes, heptanes octanes, cyclohexane, methylcyclohexane, lactol spirits, naphtha and mineral spirits.

The dispersions of this invention are fluid or semifluid compositions containing the solid in finely divided and usually deflocculated form, and can be used for any purpose for which dispersions of these particular solids are conventionally used. Thus the pigment dispersions are of value in the manufacture of printing inks particularly publication gravure and packaging inks by incorporating the dispersions with the other components conventionally used in the manufacture of such inks. Typically such inks will contain a pigment dispersed in an ink vehicle such as a liquid petroleum hydrocarbon solution of the ink, plus resin and 1-20 wt % of the quaternized oligourethane of this invention. These dispersions are also of value in the manufacture of paints, for which purpose the dispersions are incorporated into conventional alkyd or other resins.

The dyestuff dispersions are useful in the preparation of textile printing inks or solvent dyeing systems and particularly where the dyestuff is a sublimable disperse dyestuff useful in transfer printing. Inks and paints containing such dispersions are further features of the present invention.

The process for preparing the novel quaternized oligourethanes of this invention will depend on whether it is desired to make a product wherein X in the general formula above is to be the amide radical

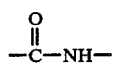

or the urethane radical

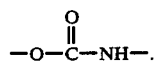

If a product is desired with the amide radical, then the 3-step process outlined below is followed. If a product containing the urethane radical is desired, then the 2-step process outlined below is followed.

The 3-step process involves:
(a) reacting a $C_2$–$C_{18}$ hydroxyalkanoic acid or a $C_3$–$C_{18}$ hydroxyalkenoic acid with rosin in the presence of an esterification catalyst,
(b) reacting the ester resulting from step (a) with a $C_{11}$–$C_{21}$ hydroxyethylimidazoline and a $C_6$–$C_{14}$ polyisocyanate;
(c) quaternizing the oligourethane resulting from step (b) by reacting it with a $C_1$–$C_4$ linear or branched alkyl halide, alkyl nitrate, alkyl phosphate, alkyl phosphite, alkyl sulfate, aryl sulfonate, alkyl sulfonate or a mineral acid or halogen acid.

The acid may be a $C_3$–$C_{18}$ hydroxyalkenoic acid such as 4-hydroxybutenoic acid, 4-hydroxy-3-pentenoic acid, castor fatty acid 6-hydroxy-3-hexenoic acid and the like, but is preferably a $C_6$–$C_{18}$ hydroxyalkanoic acid such as commercial 12-hydroxystearic acid, w-hydroxycaproic acid, glycolic acid, 4-hydroxybutyric acid, 10-hydroxydecanoic acid, 2-hydroxyisocaproic acid and the like are also useful. As for the rosin, it is preferably tall oil rosin, although wood rosin or gum rosin are also useful.

The esterification reaction is carried out in the presence of an esterification catalyst generally at elevated temperatures in the range of about 170° to 210° C. for about 8 to 18 hours. Useful esterification catalysts include dibutyltin oxide, tetrabutyl titanate, triphenylphosphite, p-toluenesulfonic acid, sulfuric acid, etc. Typically, the ratio of acid to rosin will be in the range of 1 to 6 moles of acid per mole of rosin. It is preferred that the relative proportions of acid and rosin be selected such that each oligomer molecule will contain up to one carboxyl group and the degree of esterification is between $n=1$ to $n=6$. The resultant carboxyl-terminated polyester will have a typical acid value of 70+5 mg KOH/g sample.

In step (b), 0.2–0.8 mole of ester from step (a) is reacted with 0.8–0.2 mole of the hydroxyethylimidazoline as well as with 0.8–1.0 mole of polyisocyanate. Desirably, this reaction is carried out in the presence of a catalyst such as stannous octoate. Preferred hydroxyethylimidazolines include 1-hydroxyethyl-2-heptadecenyl imidazoline, 1-hydroxyethyl-2-heptadecyl imidazoline, 1-hydroxyethyl-2-pentadecyl imidazoline, 1-hydroxyethyl-2-tridecylimidazoline and the like. Preferred polyisocyanates include mixed 2,6- and 2,4-tolylene diisocyanates, tris(4-isocyanatophenyl)methane, 4,4'-diisocyanatodiphenylmethane, hexamethylenediisocyanate, 4,4'-diisocyanatodicyclohexylmethane, phenyldiisocyanate, and the like. The reaction mixture of step (b) is maintained at a temperature of 95° to 100° C. for 2 to 5 hours.

The oligourethane resulting from step (b) is then quaternized in step (c). Quaternization is desirable since it introduces a polar or ionic cluster to one end of the non-polar chain of the oligourethane. The polar (i.e. ionic) end attaches to the pigment particle while the non-polar end serves to sterically repel other similarly-coated particles, thus preventing aggregation (or flocculation) while at the same time permitting high loadings of pigment in the dispersion. Generally the quaternizing reagent mentioned above will be utilized in a molar ratio of 0.95 to 1.0 mole per mole of tertiary nitrogen in the oligourethane. Suitable quaternizing agents include $C_1$–$C_4$ linear or branched alkyl sulfates, phosphates, phosphites, halides or nitrates phosphoric acid, nitric acid, hydrochloric acid, hydrobromic acid, hydroiodic acid, p-toluenesulfonic acid and sulfuric acid esters (which are particularly preferred).

The two-step process resulting in an oligourethane containing the urethane radical is as follows:
(a) reacting a $C_3$–$C_{18}$ linear or branched alkyl, aryl, alkaryl, aralkyl, cycloalkyl monofunctional alcohol or a monofunctional alcohol containing the radical $$R'''-OCH_2CH- \atop Y \quad m$$

with a $C_{11}-C_{17}$ hydroxyethylimidazoline and a $C_6-C_{14}$ polyisocyanate; and (b) quaternizing the oligourethane resulting from step (a) by reacting it with a $C_1-C_4$ linear or branched alkyl halide, alkyl nitrate, alkyl phosphate, alkyl phosphite, alkyl sulfate, aryl sulfonate, alkyl sulfonate or a mineral acid or halogen acid.

Suitable examples of alcohols to be employed in step (a) include hydroabietyl alcohol, butoxytriglycol and isostearyl alcohol. The hydroxyethylimidazolines and polyisocyanates are the same as those indicated above for step (b) in the 3-step process described above. The molar ratios of alcohol to hydroxyethylimidazoline and polyisocyanate are the same as in the case of the molar ratios of the ester to hydroxyethylimidazoline and the polyisocyanate; the molar ratio range of quaternizing agent to moles of tertiary nitrogen in the oligourethane is the same irrespective of whether the oligourethane is prepared by the 3-step process or the 2-step process.

This invention is illustrated but not limited by the following Examples in which the parts and percentages are by weight:

EXAMPLE 1

STEP A

Into a 4-neck reaction flask were charged 75.5 g 12-hydroxystearic acid, 24.4 g tall oil rosin and 0.1 g dibutyl tin oxide. A nitrogen blanket was maintained over the reaction mixture which was heated to 200° C. with agitation. The water of reaction was removed using a Dean and Stark trap and the heating with agitation was continued at 200°-205° C. for about 10 hours until an ester having an acid value of about 70 mg KOH/g was obtained.

STEP B

To 42.5 of the ester obtained from step A were added 19.2 g 1-hydroxyethyl-2-heptadecenyl imidazoline, 0.08 g stannous octoate and 30 g of heptane solvent. The reactants were warmed to reflux temperature with agitation while continuing the nitrogen blanket. When a solution resulted, it was heated to 95°-100° C. and 5.5 g tolylene diisocyanate gradually added, while maintaining the temperature at about 100° C. The reaction was complete after about 3 hours as indicated by the absence of the isocyanate peak at 4.45 microns under infrared spectrophotometry. The amine value of the resulting oligourethane was then measured to determine the required amount of quaternization agent.

STEP C

The oligourethane obtained in step B was quaternized with 2.8 g of diethyl sulfate. The quaternization reaction was carried out, with agitation and a nitrogen blanket, at a temperature of 95°-100° C. with the diethyl sulfate added over about a two hour period. An amine value of 1.0 mg KOH/g indicated completion of the reaction. The product was discharged upon cooling to about 45° C. and was strained through a nylon bag-type filter. The product had a viscosity of about 50 poises at 25° C. by Gardner tube, a varnish standard color of 12, a solids content of 70% N.V. in heptane and a specific gravity of 0.89.

EXAMPLE 2

Example 1 was repeated with a modification in that polyethylene glycol 200 was also added to the reactants in step B. The reaction mixture for step B was as follows:

| | |
|---|---|
| Example I - step A ester | 28.2 g |
| oleyl imidazoline | 25.5 g |
| polyethylene glycol 200 | 2.1 g |
| stannous octoate | 0.1 g |
| heptane solvent | 30.0 g |

The reactants listed above were heated and agitated in the same manner as in Example 1 and 7.7 g tolyl diisocyanate were gradually added, while maintaining the temperature at about 100° C. In step C, quaternization required 6.4 g of diethyl sulfate indicating a higher degree of quaternization in the final product.

EXAMPLE 3

15.3 parts of the quaternized oligourethane solution from Step (c) of Example 1 were dispersed in an Eiger mill with 27.7 parts heptane, 7.0 parts n-butyl alcohol and 50.0 parts of cyan blue pigment. The dispersion particle size was too fine to be measured on a grind gauge and was of the order of 0.2-0.3 micrometers. 18.5 parts of this dispersion were mixed for 5 minutes in an Ultra Turrax Mill with 9.8 parts of polyvinylchloride copolymer resin and 7.5 parts polyester plasticizer, 1.0 part wax, 48.2 parts n-propylacetate and 15.0 parts isopropylacetate. The resultant ink, after being printed on a polyester film, showed a much stronger color development than a comparable ink at the same pigment level but which did not contain the quaternized oligourethane of the present solution.

EXAMPLE 4

In this example, an alcohol was employed as the starting material for the 2-step process in order to obtain a quaternized oligourethane that contained the urethane radical rather than the amide radical. 15.48 parts of hydroabietyl alcohol and 6.1 parts butoxytriglycol were mixed with 25.8 parts of 1-hydroxyethyl-2-heptadecenylimidazoline, 0.1 part stannous octoate and 29.9 parts reagent grade n-heptane in a 4-neck round bottom flask equipped with mechanical agitator, thermometer, dry $N_2$ inlet, reflux condenser and addition funnel. The mixture was heated under $N_2$ to 95°-100° C. for solution. Toluene diisocyanate, 12.208 parts, was then added dropwise at a rate so as to maintain reflux at about 100° C. After 3-hours reaction at 95°-100° C. no IR NCO absorption peak was observed at 4.45 micrometers.

10.409 parts 98% diethyl sulfate was then added dropwise over one hour at 95°-100° C. After 1-2 hours at 95°-100° C. an amine titration of 1.0 mg KOH/g indicated that quaternization was essentially complete. The solution was cooled to 40°-50° C. and strained through a nylon organdy bag filter. The solution had the following properties:

| | |
|---|---|
| Viscosity | 200-300 poises @ 25° C. |
| Color | 11 Gardner |
| Solids | 70 + 1% |

The quaternized oligourethane solution prepared as above (13.2 parts) was dispersed with 37.8 parts heptane 6.0 parts n-butyl alcohol and 43.0 parts 2B red pigment in an Eiger Mill to give a dispersion with pigment particle size between 0.2-0.3 micrometers. The dispersion was too fine to measure on a grind gauge.

The resultant red 2B dispersion (20.3 parts) was blended for 5 minutes with 28.8 parts maleic resin, 9.0 parts ethylacetate, 23.4 parts ethanol, 13.5 parts of a 35% solution of nitrocellulose and 5.0 parts wax in the Ultra Turrax Mill. The resultant ink after printing on uncoated bleached paper stock showed better color development at the same pigmentation level as an ink which did not contain the quaternized oligourethane.

EXAMPLE 5

The quaternized oligourethane solution prepared in accordance with Example 4 (10.5 parts) was dispersed in an Eiger Mill with 50.4 parts heptane, 4.8 parts n-butyl alcohol and 34.3 parts diarylide yellow pigment. The dispersion was too fine to be measured on a grind gauge and was in the range of 0.2-0.3 micrometer particle size.

The diarylide yellow pigment dispersion (24.5 parts) was mixed with 8.1 parts n-propyl alcohol, 23.0 parts isopropyl alcohol, 24.4 parts polyamide resin, 5.0 parts naphtha, 8.0 parts maleic resin, 4.0 parts wax and 3.0 parts water in an Ultra Turrax Mill in the same manner as above. The resultant ink, when printed on high slip polyethylene and polypropylene films, showed better heat resistance, better gloss and better color strength versus the same ink made at the same pigmentation level without the quaternized oligourethane of the present invention.

EXAMPLE 6

The same apparatus as described in Example 4 was employed in this example, 28.59 parts 1-hydroxyethyl-2-heptadecenylimidazoline, 16.87 parts butoxytriglycol, 0.1 part stannous octoate and 29.90 parts heptane were mixed. The mixture was heated to 95° C. under a nitrogen blanket and thereafter dropwise addition of 12.31 parts toluene diisocyanate was begun. The rate was adjusted to maintain the temperature below 100° C., and the urethanation reaction was completed in about 3 hours as noted by the absence of the NCO peak at 4.5 microns as determined on an analytical infrared spectrophotometer.

Thereafter, 11.73 parts 98% diethyl sulfate were added over one hour at 95°-100° C. After 1-2 hours at 95°-100° C., an amine value titration of less than 1.0 mg KOH/g indicated that quaternization was complete. The product was cooled to 45°-50° C. and filtered through a nylon bag filter. It had the following properties:

| Viscosity | 130-200 poises at 25° C. |
| Color | 12 Gardner |
| Solids | 70 + 1% |

EXAMPLE 7

This example employed the same apparatus and general procedure as described in the preceding examples. A quaternized oligourethane solution was prepared from 27.04 parts 1-hydroxyethyl-2-heptadecenyl imidazoline, 6.4 parts butoxytriglycol, 13.69 parts isostearyl alcohol 0.1 parts stannous octoate, 29.9 parts heptane, 12.12 parts toluene diisocyanate and 10.75 parts 98% diethyl sulfate. After the product was cooled to 45°-50° C. and cast through a nylon bag filter, it had the following properties:

| Viscosity | 120-200 poises at 25° C. |
| Color | 11 Gardner |
| Solids | 70 + 1% |

EXAMPLE 8

The procedure of Example 7 was repeated in order to obtain a quaternized oligourethane solution based on 21.5 parts 1-hydroxyethyl-2-heptadecenyl imidazoline, 27.53 parts isostearyl alcohol, 0.1 part stannous octoate, 29.9 parts n-heptane, 12.18 parts toluene diisocyanate and 8.54 parts 98% diethyl sulfate. The product after cooling exhibited the following properties:

| Viscosity | 30-50 poises at 25° C. |
| Color | 9 Gardner |
| Solids | 70 + 1% |

EXAMPLE 9

This example was carried out in order to provide material for comparative purposes and its use is shown in the table below. Using the same type of equipment as described in Example 4, 75.5 parts 12-hydroxystearic acid, 24.4 parts tall oil rosin and 0.1 part dibutyltin oxide were mixed. The mixture was heated to 200° C. and held at that point for 9-12 hours until an acid value of 69-71 mg KOH/g was obtained. To 93.5 parts of this reaction product maintained at 70° C. were added 6.5 parts polyethyleneimine. The temperature of the mixture was slowly raised to 150° C. at which point a slight exothermic reaction occurred. The reaction mixture was held an additional 4-6 hours at this temperature until an acid value of 50-55 mg KOH/g was obtained. Thereafter, the molten oligomer was cooled to 120° C. and heptane was slowly added under reflux to provide a 70% nonvolatile content solution. The solution was then cooled to 40°-50° C. cast through a nylon organdy bag filter and such solution exhibited the following properties:

| Viscosity | 5-10 poises at 25° C. |
| Color | 14-15 Gardner |
| Solids | 70 + 1% |
| Acid Value | 52.0 (on solids) |

EXAMPLE 10

In this example, various quaternized oligourethane solutions were utilized to provide the dispersions indicated in the table below. The quaternized oligourethane solutions were utilized as 70% solids solution in heptane.

TABLE I

| | Ex.1 | Ex.1 | Ex.9 | Ex.6 | Ex.7 | Ex.8 |
|---|---|---|---|---|---|---|
| Quaternized Oligourethane Source | | | | | | |
| Quaternized Oligourethane Amount | 16.3 | 13.4 | 12.6 | 15.3 | 15.3 | 15.3 |
| Red Lake C | — | 44.0 | 41.3 | — | — | — |

TABLE I-continued

| | | | | | | |
|---|---|---|---|---|---|---|
| Carbon Black | 50.0 | — | — | — | — | — |
| Bon Pigment | — | — | — | 50.0 | — | — |
| Bon Red Pigment | — | — | — | — | — | 50.0 |
| Cyan Blue | — | — | — | — | 50.0 | — |
| Heptane | 26.7 | 36.6 | 40.3 | 27.7 | 27.7 | 27.7 |
| n-Butyl Alcohol | 7.0 | 6.0 | 5.8 | 7.0 | 7.0 | 7.0 |

As is evident from the table indicated above, the quaternized oligourethane solution of Example 1 allowed a higher Red Lake C pigment loading versus comparative Example 9, while still maintaining acceptable viscosity. The table above further indicates the benefit of obtaining free-flowing dispersions at relatively high loadings of pigment, thereby presenting the ink manufacturer and user with wide formulation latitude.

We claim:

1. A dispersion of a solid in a liquid comprising a particulate solid material selected from the group consisting of a pigment or dyestuff, an organic liquid suitable as a dispersion medium for said material and as a dispersion agent, a quaternized oligourethane having the formula:

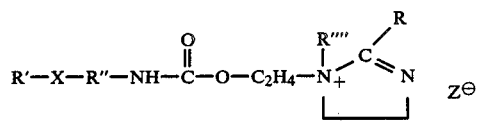

wherein X represents the radical

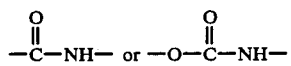

such that when X is

R' is an ester resulting from the reaction of a $C_2$–$C_{18}$ hydroxyalkanoic acid or a $C_3$–$C_{18}$ hydroxyalkenoic acid and rosin, and when X is

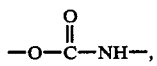

R' is a $C_3$–$C_{18}$ linear or branched alkyl, phenyl, alkaryl, aralkyl, cycloalkyl or the radical

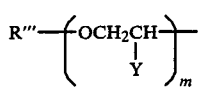

wherein Y is hydrogen or methyl, R''' is a $C_1$–$C_6$ alkyl and m is an integer of 1 to 20;

R is a $C_{11}$–$C_{17}$ linear or branched alkyl, alkenyl, alkynyl or cycloalkyl;

R'' is a $C_6$–$C_{14}$ linear or branched alkyl, phenyl, alkaryl, aralkyl or cycloalkyl or a dimer or trimer thereof;

R'''' is hydrogen or a $C_1$–$C_4$ linear or branched alkyl; and

Z is R''''$OSO_3$, Cl, Br, I, $NO_3$ R'''''$SO_3$, (R'''')$_{3-n}H_nPO_4$ or (R'''')$_{3-n}H_nPO_3$ wherein n is an integer of 0 to 3, and R''''' is phenyl, $CF_3$, $C_1$–$C_4$ linear or branched alkyl or $C_7$–$C_{12}$ aralkyl or alkaryl.

2. The dispersion of claim 1 wherein the organic liquid is an aliphatic hydrocarbon compatible with gravure and packaging ink systems.

3. The dispersion of claim 1 wherein the material is present in an amount of 30–75 wt. %, the liquid is present in an amount of 10–50 wt. % and the dispersing agent is present in an amount of 1–20 wt. %, based on the weight of the dispersion.

4. The dispersion of claim 3 wherein a nonionic surfactant is also present in an amount of up to 5 wt. %.

5. A printing ink comprising pigment dispersed in an ink vehicle comprised of a liquid petroleum hydrocarbon solution of an ink, resin and 1–20 wt. % of a quaternized oligourethane having the formula:

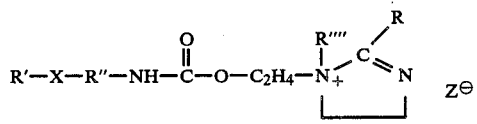

wherein X represents the radical

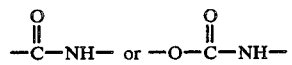

such that when X is

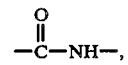

R' is an ester resulting from the reaction of a $C_2$–$C_{18}$ hydroxyalkanoic acid or a $C_3$–$C_{18}$ hydroxyalkenoic acid and rosin, and where X is

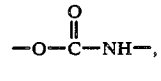

R' is a $C_3$–$C_{18}$ linear or branched alkyl, phenyl, alkaryl, aralkyl, cycloalkyl or the radical

wherein Y is hydrogen or methyl, R''' is a $C_1$–$C_6$ alkyl and m is an integer of 1 to 20;

R is a $C_{11}$–$C_{17}$ linear or branched alkyl, alkeryl, alkynyl or cycloalkyl;

R'' is a $C_6$–$C_{14}$ linear or branched alkyl, phenyl, alkaryl, aralkyl or cycloalkyl or a dimer or trimer thereof;

R'''' is hydrogen or a $C_1$–$C_4$ linear or branched alkyl; and

Z is R''''$OSO_3$, Cl, Br, I, $NO_3$ R'''''$SO_3$, (R'''')$_{3-n}H_nPO_4$ or (R'''')$_{3-n}H_nPO_3$ wherein n is an integer of 0 to 3, and R''''' is phenyl, $CF_3$, $C_1$–$C_4$ linear or branched alkyl or $C_7$–$C_{12}$ aralkyl or alkaryl.

* * * * *